United States Patent [19]

McCulloch

[11] Patent Number: 5,143,685
[45] Date of Patent: Sep. 1, 1992

[54] PROCESS FOR PURIFICATION OF ORTHO-CHLOROTOLUENE

[75] Inventor: Beth McCulloch, Barrington, Ill.

[73] Assignee: UOP, Des Plaines, Ill.

[21] Appl. No.: 290,794

[22] Filed: Dec. 28, 1988

[51] Int. Cl.$^5$ .............. C07C 17/38; C07C 7/13
[52] U.S. Cl. ..................... 570/211; 585/828
[58] Field of Search ............. 570/211; 585/828

[56] References Cited

U.S. PATENT DOCUMENTS 3,216,789 11/1965 Breck et al. ................... 23/113

OTHER PUBLICATIONS

Chen et al., *Chemical Engineering Progress*, Feb. 1988, pp. 32-40.

Primary Examiner—Marianne M. Cintins
Assistant Examiner—Michael B. Hydorn
Attorney, Agent, or Firm—Thomas K. McBride; John F. Spears, Jr.; Jack H. Hall

[57] ABSTRACT

A process for separating the ortho-isomer of chlorotoluene from a feed mixture containing ortho- and para-chlorotoluene by selective adsorption and desorption with an L zeolite adsorbent having potassium or potassium and sodium cations at cation exchange sites and a desorbent containing chlorobenzene or mixtures thereof with a saturated aliphatic hydrocarbon and especially 10-50% chlorobenzene and 50-90% saturated aliphatic hydrocarbon. The ortho-chlorotoluene is relatively non-absorbed on the adsorbent and is recovered prior to more strongly adsorbed species in a rejective separation process.

10 Claims, 1 Drawing Sheet

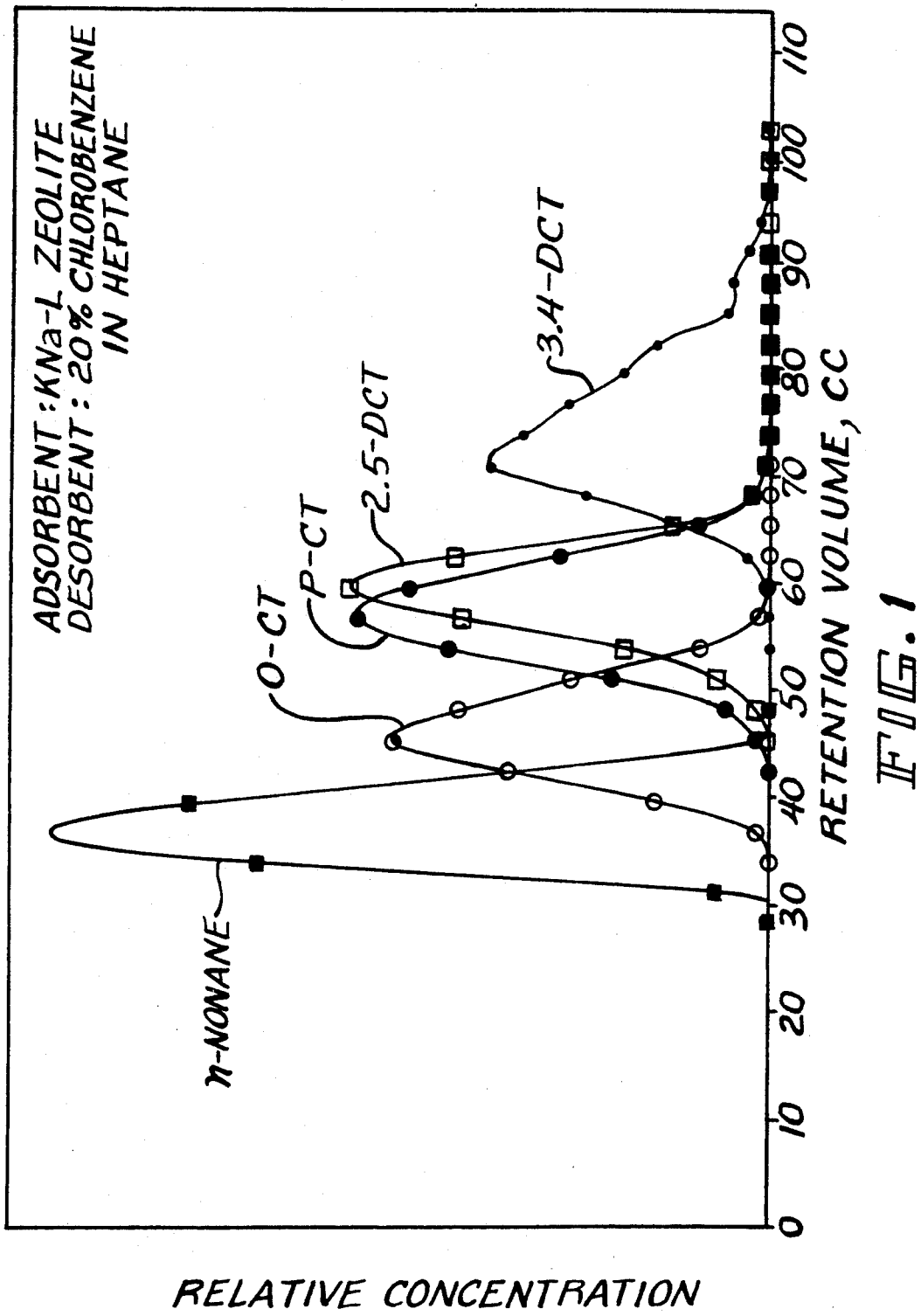

PROCESS FOR PURIFICATION OF ORTHO-CHLOROTOLUENE

BACKGROUND OF THE INVENTION

1. Field Of The Invention

The field of art to which this invention pertains is the solid bed adsorptive separation of halogen substituted aromatic hydrocarbons. More specifically, the invention relates to a process for separating para- and ortho-chlorotoluenes by adsorption chromatography with L-type zeolites.

2. Background Information

A wide variety of halogenating agents, catalysts and reaction conditions are used in processes for halogenating toluene. For example, mixtures of monochlorotoluenes are obtained by chlorination with certain Lewis acid halide catalysts, including the chlorides of aluminum, tin, titanium and zirconium, and with ferric chloride as catalyst. Other methods of obtaining monochlorotoluene isomers include the non-catalytic nuclear chlorination of toluene in various solvents, and the use of hydrogen chloride as a chlorinating agent in both liquid and vapor phase systems. In some cases, the mixture of monochlorotoluenes may contain more than 70% of the orthoisomer. However, considerable para-isomer content is also obtained, which in certain applications is detrimental to further utilization of the ortho-chlorotoluene product. When preparing monochlorotoluene isomers by direct chlorination routes, it has been found that less than 1% of the isomers produced will comprise the meta isomer, except that the meta isomer may comprise up to about 2% with ferric chloride. Consequently, feedstocks for this invention will often contain a small proportion of the meta isomer which is not removed prior to the separation of the para- and orthoisomers.

Chlorotoluenes are important as chemical intermediates. Both mono-and dichlorotoluenes are used in the manufacture of pesticides, dye stuffs, pharmaceuticals and peroxides. Halogen substituted toluenes are also employed as solvents.

One application for highly pure ortho-chlorotoluene (o-CT) is in the further chlorination of o-CT by the same routes mentioned above to obtain a mixture of dichlorotoluene (DCT) isomers, i.e., 2,3-, 2,4-, 2,5- and 2,6-DCT, from which 2,5-DCT can be separated chromatographically with alkali metal-exchanged L zeolites as disclosed in McCulloch et al U.S. Pat. No. 4,922,040 However, if the o-CT feed is contaminated with para-chlorotoluene (p-CT), 3,4-DCT is additionally formed. 3,4-DCT and any unreacted p-CT cannot be easily separated from the 2,5-DCT extract product by either simple fractionation or by the chromatographic separation referred to in said application since 3,4-DCT and p-CT are also adsorbed by the L zeolite. Hence, the purity of the 2,5-DCT product of the latter separation process is lowered to the extent that p-CT contaminates the o-CT being chlorinated.

Separation of ortho-chlorotoluene (bp 157°-59° C.) and para-chlorotoluene (bp 162° C.) is difficult due to the close boiling point range of these isomers. In order to accomplish a separation of these isomers by fractionation, it is necessary to use a high efficiency isomer separation column. This invention simplifies the separation procedure by providing a more effective adsorptive separation method.

Japanese Patent Application Nos. 11,884/82 and 50,440/83 deal with the separation of meta-chlorotoluene (m-CT) from a mixture of chlorotoluene isomers. In the first application, m-CT is adsorbed on a Y zeolite containing silver and potassium cations. The second application teaches the separation of m-CT from o-CT and p-CT on a Y zeolite adsorbent containing sodium and copper cations as essential components.

The separation of halogenated aromatic isomers using X zeolites containing alkali metal or alkaline earth metal cations is disclosed and exemplified in Fleck et al U.S. Pat. No. 2,958,708 and Japanese Patent Publication 5155/60. Japanese No. 5155/60 further discloses the use of chlorobenzene as desorbent.

U.S. Pat. No. 4,605,799 discloses the adsorptive separation of halogenated toluenes, e.g., a mixture of chlorotoluene isomers with a Y-type zeolite exchanged with sodium or potassium cations and a desorbent such as 3,4-dichlorotoluene.

I have found an adsorbent, which, in combination with certain desorbent liquids, will selectively adsorb all the chlorotoluene isomers, except o-CT, which is relatively non-adsorbed and which elutes near the void. Thus, the largest component of the feed, o-CT is eluted as raffinate and the minor components are adsorbed and eluted as extract by desorption with the desorbent. This so-called rejective separation of the major components is desirable since utilities are lower and adsorbent capacity requirement for the adsorbed components is lower per unit of output product. Another advantage of the present invention is that the separation can be accomplished with the same adsorbent/desorbent combination used for the separation of the dichlorotoluene chlorination products of o-CT, i.e., as disclosed in the aforementioned U.S. Pat. No. 4,922,040.

Methods for forming the crystalline powders into agglomerates are also known and include the addition of an inorganic binder, generally a clay comprising a silicon dioxide and aluminum oxide, to a high purity zeolite powder in wet mixture. The blended clay zeolite mixture is extruded into cylindrical type pellets or formed into beads which are subsequently calcined in order to convert the clay to an amorphous binder of considerable mechanical strength. Clays of the kaolin type, water permeable organic polymers and silica may also be used as binders.

The invention herein can be practiced in fixed or moving adsorbent bed systems, but the preferred system for this separation is a countercurrent simulated moving bed system, such as described in Broughton U.S. Pat. No. 2,985,589, incorporated herein by reference. Cyclic advancement of the input and output streams can be accomplished by a manifolding system, which are also known, e.g., by rotary disc valves shown in U.S. Pat. Nos. 3,040,777 and 3,422,848. Equipment utilizing these principles are familiar, in sizes ranging from pilot plant scale (deRossett U.S. Patent 3,706,812) to commercial scale in flow rates from a few cc per hour to many thousands of gallons per hour.

The functions and properties of adsorbents and desorbents in the chromatographic separation of liquid components are well-known, but for reference thereto, Zinnen et al U.S. Pat. No. 4,642,397 is incorporated herein.

It has now been discovered that L-type zeolites having potassium cations or a mixture of sodium and potassium cations at cation exchange sites are suitable adsorbents for the separation of ortho-chlorotoluene (o-CT) from other isomers of chlorotoluene.

SUMMARY OF THE INVENTION

In brief summary, the invention is a process for separating the para- and ortho-isomers of chlorotoluene or bromotoluene from a feed mixture comprising a mixture of the isomers. Referring for convenience hereafter to chlorotoluene or one of the isomers thereof, it is understood that bromotoluene and its isomers are also intended. The process comprises contacting the feed mixture at adsorption conditions with an adsorbent comprising an L-type zeolite containing potassium cations or potassium and sodium cations at cation exchange sites. After contact with the adsorbent, the o-CT, the relatively unadsorbed portion of the feed, is removed in a rejective separation process from the adsorbent as raffinate product. The adsorbed component, p-CT, is recovered using a desorbent mixture comprising chlorobenzene or chlorobenzene diluted with a saturated aliphatic hydrocarbon. In a more specific embodiment, the desorbent comprises 10-50 volume percent chlorobenzene in admixture with a saturated aliphatic hydrocarbon having less than nine carbon atoms, e.g., n-heptane.

The general scheme for such, a rejective adsorption separation is described in Zinnen et al U.S. Pat. No. 4,940,830 incorporated herein by reference. Briefly, the less adsorbed feed component(s) is eluted from the nonselective void volume and weakly adsorbing volume before the more strongly adsorbed component(s). The relatively unadsorbed component(s) is thereby recovered in the raffinate. A particular advantage of such a system lies where the unadsorbed fraction or component is large in relation to the other fraction or components, since substantially less adsorbent and smaller sized equipment is required for a given feed throughout than if the large fraction is selectively adsorbed on the adsorbent.

Preferred feed mixtures for this process contain substantial quantities of the para- and ortho-isomers of monohalotoluenes and little or no meta-halotoluene.

To separate the ortho-isomer from a feed mixture comprising monochlorotoluenes in accordance with the present invention, the mixture is contacted with the previously mentioned class of adsorbents and the para-isomer is selectively adsorbed and retained by the adsorbent while the relatively unadsorbed ortho-isomer is removed from the interstitial void spaces between the particles of adsorbent and the surface of adsorbent. The more selectively adsorbed isomer(s) can then be removed from the adsorbent with a desorbent material. Both isomer products can be fractionated to separate the desorbent and recycle it to the process.

In the process of this invention, it has been found that particular desorbent materials, comprising chlorobenzene or mixtures of chlorobenzene and a saturated aliphatic hydrocarbon, provide good selectivity in the adsorptive separation of bromo- or chlorotoluene isomers with the adsorbents herein described. Of the aliphatic hydrocarbons which may be used in the desorbents, those having four to eight carbon atoms are most useful due to their lower boiling point properties. Of these hydrocarbons, n-heptane is preferred. Moreover, suitable desorbents will contain from 10-50 volume percent of the chlorobenzene. A particularly preferred desorbent is 20 volume percent chlorobenzene and 80 volume percent n-heptane. Chlorobenzene or mixtures thereof with saturated aliphatic hydrocarbons in concentrations less than 50% are expected to provide adequate selectivity for chlorotoluene isomers when the K-L adsorbent has been partially exchanged with sodium cations.

Other embodiments of the present invention encompass specific feed mixtures, desorbent compositions, flow schemes and operating conditions, all of which are hereinafter disclosed in the following discussion of the present invention.

BRIEF DESCRIPTION OF THE DRAWING

The drawing is a chromatographic trace of the pulse test of the Example showing the separation of ortho-chlorotoluene with a KNa-L zeolite adsorbent.

DETAILED DESCRIPTION OF THE INVENTION

Adsorbents to be used in the process of this invention will comprise specific crystalline aluminosilicates or molecular sieves, namely, L zeolites. The L zeolite structure contains alumina and silica tetrahedra which are intimately connected with additional oxygen atoms in a network to form one-dimensional channels. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions and thus the crystalline aluminosilicates are often referred to as "molecular sieves." In the present invention, the water content of the adsorbent, based on loss on ignition (L.O.I.) is from 0.1 to 20% (wt.), preferably 0.5% (wt.).

The L zeolite in the hydrated or partially hydrated form may be represented in terms of moles of oxides as in Formula 1 below:

$$(0.9-1.3)M_{2/n}O:Al_2O_3:(5.2-6.9)SiO_2:yH_2O \qquad \text{Formula 1}$$

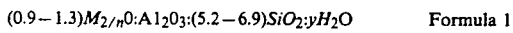

where M designates at least one exchangeable cation as defined below, n is the valence of M and y may be any value from 0 to about 9. It is preferred to synthesize the potassium form of the L-type zeolite since the reactants to make this form are readily available and generally water soluble. Thus, the as-made form of the L zeolite is referred to as potassium-L, or K-L, zeolite. L zeolite is characterized by planar 12-ring pores aligned to produce one-dimensional channels, linked to each other by small pore openings which will not admit water molecules. A minor two-dimensional pore system also exists, parallel to the aforesaid channels. For further description of the L zeolites, see Breck, *Zeolite Molecular Sieves-Structure, Chemistry, and Use*, John Wiley & Sons, New York, 1974, pp 156, and Breck et al U.S. Pat. No. 3,216,789, which si incorporated herein by reference.

Although the separation can be accomplished with K-L zeolite adsorbent, I prefer the potassium ions partially or, to the fullest extent possible, exchanged by sodium. The preferred mixed NaK-L zeolite is in the range of 1 to 3 percent sodium, with potassium remaining in exchangeable sites about 8 to 12.2 wt. %. In the as-formed state, potassium level is about 13.0 wt. %.

The adsorbent may be supported by an inorganic matrix material such as silica, titania, or alumina or mixtures thereof, or compounds, such as clays, which material is present in intimate mixture with the small particles of the zeolite material. This matrix material, or binder, typically in amounts ranging from 2-25 wt. % aids in forming or agglomerating the particles and may be an adjunct of the manufacturing process for zeolite, (for example, intentionally incomplete purification of the zeolite during its manufacture) or it may be added to relatively pure zeolite. Normally, the adsorbent will be in the form of particles such as extrudates, aggregates, tablets, macrospheres or granules having a desired particle size range. The typical adsorbent will have a particle size range of about 16-60 mesh (Standard U.S. Mesh).

Although it is not clear what properties of the adsorbent are responsible for the separation of dichlorotoluene isomers herein described, it appears that it cannot be attributed to pore size selectivity alone. Since the isomers being separated are of similar size, it appears that stearic factors may play a more important role in the separation than electrostatic attraction. Since ortho-chlorotoluene, which is the most polar CT isomer, is not adsorbed by L zeolite contrary to the selectivity of X and Y faujasite-type zeolites, it is theorized that the one-dimensional channel structure of L zeolite is responsible for the unexpected performance in separating chlorotoluenes as compared to faujasites, which exhibit a three-dimensional open cage structure.

L zeolites with potassium cations at the cation exchange sites possess the selectivity and other necessary requirements for use in our process; however, a potassium L-type zeolite, partially exchanged with sodium is particularly preferred.

In this process, and particularly the preferred continuous simulated moving bed process, the desorbent must be selected to satisfy the following criteria: First, the desorbent material should displace an extract component from the adsorbent with reasonable mass flow rates without itself being so strongly adsorbed as to unduly prevent an extract component from displacing the desorbent material in a following adsorption cycle. Secondly, the desorbent material must be compatible with the particular adsorbent and the particular feed mixture. More specifically, it must not reduce or destroy the critical selectivity of the adsorbent for an extract component with respect to a raffinate component. The desorbent should additionally be easily separable from the feed mixture that is passed into the process. Both the raffinate stream and the extract stream are removed from the adsorbent in admixture with desorbent material and without a method of separating at least a portion of the desorbent material, the purity of the extract product and the raffinate product would not be very high nor would the desorbent material be available for reuse in the process. It is, therefore, contemplated that any desorbent material used in this process will preferably have a substantially different average boiling point than that of the feed mixture, i.e., more than about 5° C. difference, to allow separation of at least a portion of desorbent material from feed components in the extract and raffinate streams by simple fractional distillation, thereby permitting reuse of desorbent material in the process. Finally, desorbent materials should also be materials which are readily available and, therefore, reasonable in cost. However, a suitable desorbent or desorbents for a particular separation with a specific adsorbent are not always predictable. In the preferred isothermal, isobaric, liquid-phase operation of the process of my invention, a desorbent material comprising 10-50 volume percent chlorobenzene and 50-90 volume percent of a saturated aliphatic hydrocarbon having less than nine carbon atoms will result in good selectivity for the adsorbed p-CT isomer when used with the above discussed adsorbents, but it is expected that the aforesaid mixtures with up to, and including, 100% chlorobenzene will be satisfactory with the preferred NaKL zeolite adsorbent.

A typical feed mixture which can be separated in the process of this invention resulting from the chlorination of toluene contains the following mixture of isomers: 90% (wt) ortho-chlorotoluene, 8% (wt) para-chlorotoluene and less than 2% (wt) meta-chlorotoluene and other unidentified materials.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor phase operation. Adsorption conditions will include a temperature range of from about 110° C. to about 200° C., with about 150° C. to about 180° C. being preferred and a pressure sufficient to maintain liquid-phase, ranging from about atmospheric to about 500 psig, with from about atmospheric to about 200 psig usually being adequate. Desorption conditions will include the same range of temperatures and pressures as used for adsorption conditions.

At least a portion of the raffinate stream, which contains the concentrated o-CT product, and preferably at least a portion of the extract stream, from the separation process are passed to separation means, typically fractionators or evaporators, where at least a portion of desorbent material is separated to produce a raffinate product and an extract product, respectively.

A dynamic testing apparatus is employed to test various adsorbents with a particular feed mixture and desorbent material to measure the adsorption characteristics of retention, capacity and exchange rate. The apparatus consists of a helical adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect qualitatively, or determine quantitatively, one or more components in the effluent stream leaving the adsorbent chamber. A pulse test, performed using this apparatus and the following general procedure, is used to determine data, e.g., selectivity, for various adsorbent systems. The adsorbent is placed in a chamber and filled to equilibrium with a particular desorbent material by passing the desorbent material through the adsorbent chamber. At a convenient time, a pulse of feed containing known concentrations of a tracer and of a particular extract component or of a raffinate component or both, all diluted in desorbent material is injected for a duration of several minutes. Desorbent material flow is resumed, and the tracer and the extract component or the raffinate component (or both) are eluted as in a liquid-solid chromatographic operation. The effluent can be analyzed on-stream or, alternatively, effluent samples can be collected periodically and later analyzed separately by analytical equipment and traces of the envelopes or corresponding component peaks developed.

From information derived from the test, adsorbent performance can be rated in terms of void volume, retention volume for an extract or a raffinate component, the rate of desorption of an extract component from the adsorbent and selectivity. The retention volume of an extract or a raffinate component may be characterized by the distance between the center of the peak envelope of the extract or raffinate component and the center of the peak envelope of the tracer component (void volume) or some other known reference point. It is expressed in terms of the volume in cubic centimeters of desorbent material pumped during this time interval represented by the distance between the peak envelopes. The rate of exchange or desorption rate of an extract component with the desorbent material can generally be characterized by the width of the peak envelopes at half intensity. The narrower the peak width, the faster the desorption rate. Selectivity, $\beta$, is determined by the ratio of the net retention volumes of the more strongly adsorbed component to each of the other components.

The examples shown below are intended to further illustrate the process of this invention without unduly limiting the scope and spirit of said process.

EXAMPLE

A pulse test as described above was performed to evaluate the process of the present invention for separating ortho-chlorotoluene from para-chlorotoluene. The column was filled with 70 cc of K-L zeolite partially exchanged with sodium cations at cation exchange sites and maintained at a temperature of 150° C. and a pressure sufficient to provide liquid-phase operations. The feed mixture employed for this test contained 2.5 volume percent each of orthochlorotoluene, para-chlorotoluene, 3,4-dichlorotoluene, 2,5-dichlorotoluene, 1 volume percent normal nonane and the remainder (89%) desorbent material. The desorbent material was 20 weight percent chlorobenzene in n-heptane. The desorbent material was run continuously at a nominal liquid hourly space velocity (LHSV) of 1 which amounted to about 1.42 cc per minute flow rate of desorbent. At some convenient time interval the desorbent was stopped and the feed mixture was run for a 3.5 minute interval at a rate of 1.42 cc per minute. The desorbent stream was then resumed at 1 LHSV and continued to pass into the adsorbent column until all of the feed components had been eluted from the column as determined by observing the chromatograph generated by the effluent material leaving the adsorption column. The sequence of operations usually takes about an hour. The chromatograph tracing obtained is shown in FIG. 1. The ortho-chlorotoluene product is removed as raffinate at the said volume with a very satisfactory degree of separation from the adsorbed components of the feed. The results are also set forth in the following table of retention values and selectivities ($\oplus$).

TABLE

| Component | GRV | NRV | beta($\beta$) |
|---|---|---|---|
| n-Nonane | 37.7 | 0.0 | tracer |
| o-CT | 46.3 | 9.3 | 4.17 |
| p-CT | 57.3 | 20.3 | 1.83 |
| 2,5-DCT | 59.5 | 22.5 | 1.65 |
| 3,4-DCT | 73.6 | 36.6 | reference |

We claim as our invention:

1. A process for separating ortho-chlorotoluene from a feed mixture comprising ortho-chlorotoluene and para-chlorotoluene which process comprises contacting said feed mixture at adsorption conditions, with an adsorbent comprising an L zeolite having potassium cations or mixtures thereof with sodium at cation exchange sites, selectively adsorbing said para-chlorotoluene in preference to said ortho-chlorotoluene and removing the relatively nonadsorbed ortho-chlorotoluene from contact with the adsorbent.

2. The process of claim 1 in which said adsorbed isomers are desorbed by contacting the adsorbent with a desorbent, at desorption conditions, said desorbent comprising chlorobenzene alone, or in admixture with a saturated aliphatic hydrocarbon.

3. The process of claim 2, wherein the selectively adsorbed para-chlorotoluene isomer is desorbed and said desorbent comprises a mixture of from 10 to 50% (vol) chlorobenzene and from 50 to 90% (vol) of a saturated aliphatic hydrocarbon.

4. The process of claim 3 wherein said saturated aliphatic hydrocarbon contains from four to eight carbon atoms.

5. The process of claim 4, wherein said saturated aliphatic hydrocarbon is n-heptane.

6. The process of claim 1 wherein the temperature and pressure of said adsorption conditions include a temperature in the range of about,110° C. to about 250° C. and a pressure sufficient to maintain liquid-phase.

7. The process of claim 1 wherein the separation is effected by a simulated moving bed system.

8. The process of claim 7 wherein the simulated moving bed uses a countercurrent system.

9. A process for the separation of ortho-chlorotoluene from a feed mixture comprising ortho-chlorotoluene and para-chlorotoluene which process comprises contacting said feed mixture, at adsorption conditions, with an adsorbent comprising an L zeolite having potassium cations at cation exchange sites partially replaced by sodium cations, selectively adsorbing para-chlorotoluene, removing the relatively nonadsorbed portion of the feed mixture from contact with the adsorbent recovering said para-chlorotoluene by contacting the para-chlorotoluene containing adsorbent, at desorption conditions, with a desorbent material comprising a mixture of 10 to 50 volume percent of a saturated aliphatic hydrocarbon having less than nine carbon atoms, and thereafter recovering ortho-chlorotoluene form said nonadsorbed portion.

10. The process of claim 9, where said aliphatic hydrocarbon comprises n-heptane.

* * * * *